US008585286B2

(12) United States Patent
Livne et al.

(10) Patent No.: US 8,585,286 B2
(45) Date of Patent: Nov. 19, 2013

(54) SPECTRAL DETECTOR CALIBRATION

(75) Inventors: Amir Livne, Zichron Yaaqov (IL); Naor Wainer, Zichron Yaaqov (IL); Jens-Peter Schlomka, Hamburg (DE); Ewald Roessl, Ellerau (DE); Roland Proksa, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 296 days.

(21) Appl. No.: 12/934,661

(22) PCT Filed: Mar. 20, 2009

(86) PCT No.: PCT/IB2009/051189
§ 371 (c)(1),
(2), (4) Date: Sep. 27, 2010

(87) PCT Pub. No.: WO2009/122317
PCT Pub. Date: Oct. 8, 2009

(65) Prior Publication Data
US 2011/0012014 A1    Jan. 20, 2011

Related U.S. Application Data

(60) Provisional application No. 61/041,256, filed on Apr. 1, 2008, provisional application No. 61/106,241, filed on Oct. 17, 2008.

(51) Int. Cl.
*G01D 18/00* (2006.01)
(52) U.S. Cl.
USPC ............................... 378/207; 378/44

(58) Field of Classification Search
USPC ...................... 378/4–20, 44–56, 207
See application file for complete search history.

(56) References Cited

U.S. PATENT DOCUMENTS

| 3,766,383 | A | | 10/1973 | Harris |
| 4,097,736 | A | | 6/1978 | Jacobson et al. |
| 4,843,619 | A | | 6/1989 | Sheridan |
| 5,768,334 | A | * | 6/1998 | Maitrejean et al. ............ 378/53 |
| 6,043,486 | A | * | 3/2000 | Hossain ................... 250/252.1 |
| 2005/0220265 | A1 | * | 10/2005 | Besson .......................... 378/16 |
| 2009/0310744 | A1 | * | 12/2009 | Petch et al. .................... 378/53 |

FOREIGN PATENT DOCUMENTS

EP    0338233 A2    10/1989
WO    2008007976 A1    1/2008

OTHER PUBLICATIONS

Schlomka, J. P., et al.; Experimental feasibility of multi-energy photon-counting K-edge imaging in pre-clinical computed tomography; 2008; Phys. Med. Biol.; 53:4031-4047.

* cited by examiner

*Primary Examiner* — Hoon Song

(57) ABSTRACT

A method includes detecting radiation that traverses a material having a known spectral characteristic with a radiation sensitive detector pixel that outputs a signal indicative of the detected radiation and determining a mapping between the output signal and the spectral characteristic. The method further includes determining an energy of a photon detected by the radiation sensitive detector pixel based on a corresponding output of the radiation sensitive detector pixel and the mapping.

30 Claims, 9 Drawing Sheets

SPECTRAL DETECTOR CALIBRATION

CROSS REFERENCE TO RELATED APPLICATIONS

This application claims the benefit of U.S. provisional application Ser. No. 61/041,256 filed Apr. 1, 2008 and U.S. provisional application Ser. No. 61/106,241 filed Oct. 17, 2008, both of which are incorporated herein by reference.

The following generally relates to calibrating a radiation sensitive detector, and finds particular application to computed tomography (CT). However, it also amenable to other medical imaging applications and to non-medical imaging applications.

A computed tomography (CT) scanner has included an x-ray tube located opposite a detector array with a plurality of radiation sensitive photo-sensors. The x-ray tube emits polyenergetic ionizing (x-ray) photons that traverse an examination region (including any object/subject therein) defined between the x-ray tube and the detector array. Each of the photo-sensors detects photons that traverses the examination region and generates projection data indicative thereof. A reconstructor reconstructs the projection data to generate volumetric image data, which can be used to generate an image(s). The resulting image(s) includes pixels that typically are represented in terms of gray scale values corresponding to relative radiodensity. Such information reflects the attenuation characteristics of the scanned object/subject and generally shows the structure of the scanned object/subject.

With respect to spectral CT, the spectral characteristics of the detected radiation are also determined and used to provide further information such as metabolic information, data used to identify scanned structure, etc. Cadmium Zinc Telluride (CZT) based detector arrays as well as other spectral detector arrays detect spectral information by counting photons and measuring the energy thereof. Such a detector array, in conjunction with electronics, generates a signal (a current, charge or a voltage) that is correlated with the energy of the impingent photon. The correlation has been based on a calibration, which is performed by detecting radiation emitted from radioactive materials with narrow emission lines and known emission energies, and correlating the maximum response value in the output signal of a photo-sensor for each radioactive source with the known energy of the corresponding radioactive materials. From at least two data points, a calibration curve can be generated. This is performed for each of the photo-sensors.

Such a calibration has several drawbacks. For instance, suitable radioactive materials, such as cobalt 57 (Co57) can be relatively expensive. In addition, radioactive materials like Co57 have half-lives of less than a year and, thus, may need to be replaced every year, further increasing cost. Furthermore, there is a limit on how much radioactive activity can be concentrated in a small volume of radioactive material, and the limit on the radioactive activity limits the count rate, which may result in relatively long calibration times in order to obtain a suitable count for the calibration. Furthermore, such radioactive materials generally are regulated, requiring certification by facilities using them, and are handled by technicians with the requisite training for handling radioactive materials. Moreover, additional mechanics may be required to place and position the radioactive materials in the examination region and to remove the radioactive materials therefrom.

Aspects of the present application address the above-referenced matters and others.

According to one aspect, a method includes detecting radiation that traverses a material having a known spectral characteristic with a radiation sensitive detector pixel that outputs a signal indicative of the detected radiation and determining a mapping between the output signal and the spectral characteristic.

According to another aspect, a medical imaging system includes a radiation source that emits radiation that traverses an examination region, a spectral detector that detects radiation that traverses an examination region, and a calibration component that calibrates the spectral detector based on the detected radiation.

According to another aspect, a computer readable storage medium containing instructions which, when executed by a computer, cause the computer to perform the steps of: detecting generated radiation that traverses a material having a known spectral characteristic with a radiation sensitive detector pixel that outputs a signal indicative of the detected radiation, determining a mapping between the output signal and the spectral characteristic, and determining an energy of a photon detected by the radiation sensitive detector pixel based on a corresponding output of the radiation sensitive detector pixel and the mapping.

According to another aspect, a method for calibrating a detector array of an imaging system includes detecting fluorescence radiation having a known spectral characteristic with a radiation sensitive detector pixel of the detector array, which outputs a signal indicative of an energy of the detected fluorescence radiation, determining a mapping between the output signal and the known spectral characteristic, and determining a calibration for the detector array of the imaging system based on the mapping.

According to another aspect, an imaging system includes a radiation source that emits first radiation that traverses an examination region, a detector array detects the first radiation and generates a signal indicative thereof, and a detector calibration apparatus. The detector calibration apparatus includes a radiation block that blocks the first radiation from illuminating the detector array and at least one target that receives the first radiation and generates second radiation that includes a known spectral characteristic and that illuminates the detector array.

According to another aspect, a detector calibration apparatus includes a radiation block that blocks radiation impingent thereon and a target that receives the radiation and in response emits radiation having a known spectral characteristic, wherein the detector calibration apparatus is employed to calibrate a detector array of an imaging system.

The invention may take form in various components and arrangements of components, and in various steps and arrangements of steps. The drawings are only for purposes of illustrating the preferred embodiments and are not to be construed as limiting the invention.

Figure 1:
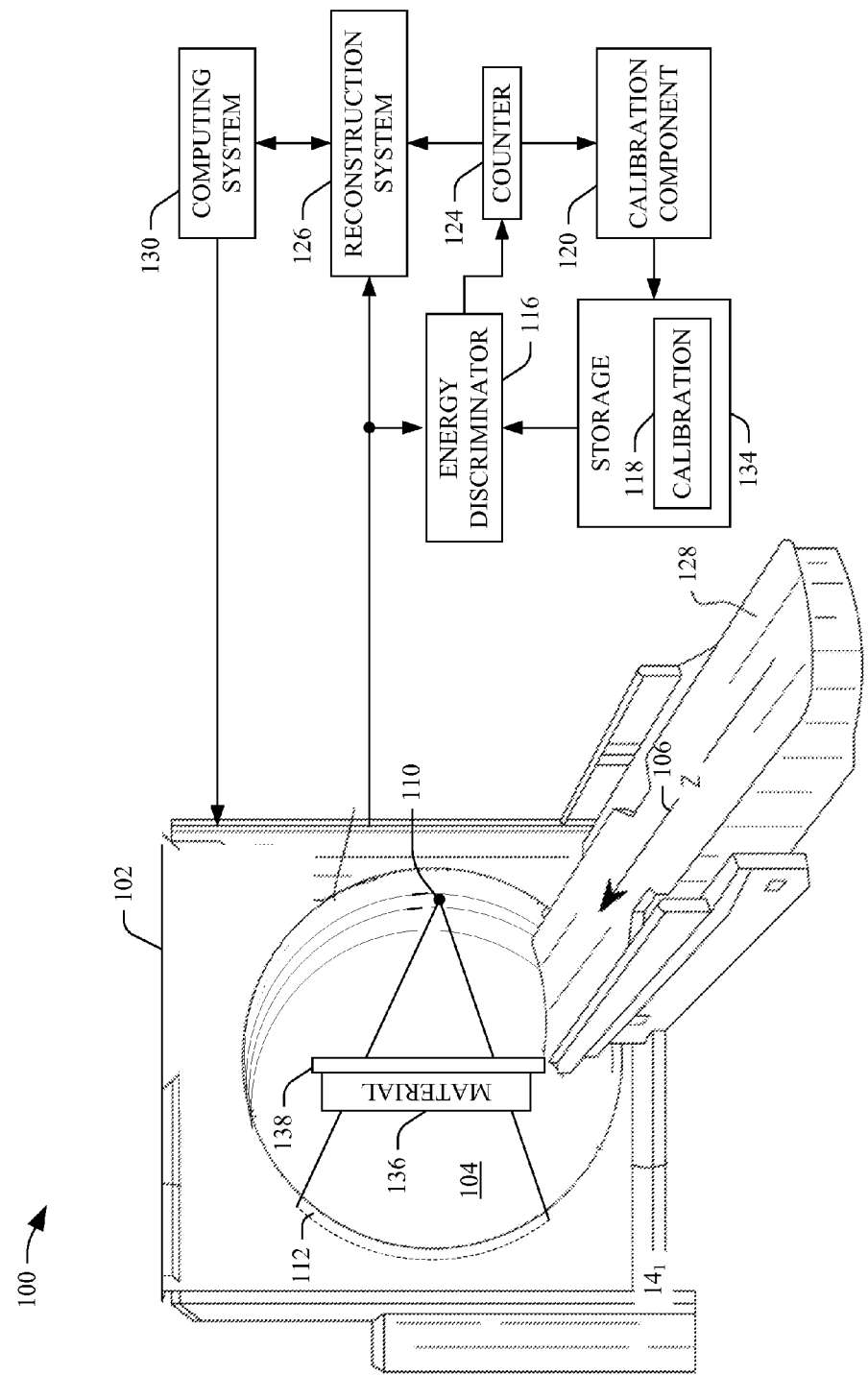
FIG. 1 illustrates an imaging system in connection with a spectral detector calibration component.

Initially referring to FIG. 1, a computed tomography (CT) scanner 100 includes a stationary gantry 102, which is stationary in the sense that it is generally stationary during scanning. However, the stationary gantry 102 may be configured to tilt and/or otherwise be moved.

The scanner 100 also includes a rotating gantry (not visible), which is rotatably supported by the stationary gantry 102. The rotating gantry rotates around an examination region 104 about a longitudinal or z-axis 106.

A radiation source 110, such as an x-ray tube, is supported by and rotates with the rotating gantry around the examination region 106. The radiation source 110 emits a generally fan, wedge, or cone shaped poly-energetic radiation beam that traverses the examination region 106.

A filter (not visible) located proximate the source 110 filters photons with energies below the diagnostic imaging range, such as photons with energies below 10 keV, from the radiation beam. Removing such photons may reduce patient dose and increases the effective energy of the beam. In one instance, the filter is located in a tray positioned near the source and can be selectively moved into and out of the radiation beam.

A detector array 112 detects photons impingent thereon and generates a signal indicative of the detected radiation. The detector array 112 includes one or more rows of radiation sensitive pixels, and each pixel generates a voltage, current or charge signal having a peak amplitude indicative of an energy of a photon detected therewith.

An energy discriminator 116 energy discriminates the signal, for example, by comparing the peak amplitude of the signal with one or more thresholds that respectively correspond to particular different energy levels. A calibration 118, which correlates the output value of the detector array 112 with an energy level of a detected photon, is used to set one or more threshold values for one or more discrimination energy levels. The energy discriminator 116 produces an output signal, for each threshold, which indicates whether a peak amplitude of the output signal exceeds the corresponding threshold. A pulse shaper and/or other electronics may be used to process and/or condition the signal output by the detector for discrimination.

A counter 124 increments a corresponding count value for a threshold when the peak amplitude of the signal exceeds the threshold. The count value for each threshold provides the number of detected photons having an energy that exceeds the corresponding threshold. The detected photons are energy binned in one or more energy bins based on the counts.

A reconstructor 126 selectively reconstructs the signals generated by the detector 112 based on the counts, which, as discussed above, are indicative of the spectral characteristics of the signals.

A patient support 128, such as a couch, supports a patient in the examination region 104. The patient support 128 is movable along the z-axis 106 in coordination with the rotation of the rotating gantry to facilitate helical, axial, or other desired scanning trajectories.

A general purpose computing system 130 serves as an operator console, which includes human readable output devices such as a display and/or printer and input devices such as a keyboard and/or mouse. Software resident on the computing system 130 allows the operator to control the operation of the system 100, for example, by allowing the operator to run a detector calibration routine, select a scan protocol, initiate and terminate scanning, view and/or manipulate the volumetric image data, and/or otherwise interact with the system 100.

As noted above, the calibration 118 correlates the output of the detector array 112 with the energy level of detected photons and is used to set appropriate thresholds based on particular energy levels of interest. A calibration component 120 generates the calibration 118, which can be stored in a storage component 134 or elsewhere. As described in greater detail below, in one instance the calibration component 120 generates the calibration 118 by detecting radiation of known energy and correlating the output signal for each pixel of the detector array 112 with the known energy for at least two different energies, and then using the resulting data points to determine the energy of a detected photon by correlating the output signal of the detector with an energy based on the data points.

Radiation of known energy is produced by placing a material 136 with a known spectral characteristic, such as a k-edge energy or other spectral characteristic, in the path of the radiation beam and detecting radiation that traverses the material 136. In the illustrated embodiment, the material 136 is shown in about the middle of the examination region 104. However, it is to be understood that this location is non-limiting in that the material 136 may alternatively be placed nearer to the source 110 or the detector 112. In one instance, the material 136 can be placed in a filter tray 138 (e.g., the filter tray used to filter low energy photons) and selectively moved into the radiation beam (e.g., during calibration) and out of the radiation beam (e.g., during a procedure). In general, at least two different materials 136 with different known spectral characteristics are used for the calibration 118. It is also to be appreciated that the at least two different materials may be in separate entities or in different regions of the same entity. The particular material 136 used may depend on a target agent of interest for a scanning procedure and/or otherwise.

Using the radiation source 110 and the material 136 to generate radiation having a known spectral characteristic mitigates various drawbacks related to using radioactive materials. By way of example, a radioactive material such as Co57 is not required, thereby mitigating the drawbacks associated with procuring, replacing and handling such a radioactive material, compensating for limited radioactive activity, obtaining certification for using such a radioactive material, and incorporating mechanics for maneuvering such a radioactive material into and out of the examination region 104.

Figure 2:
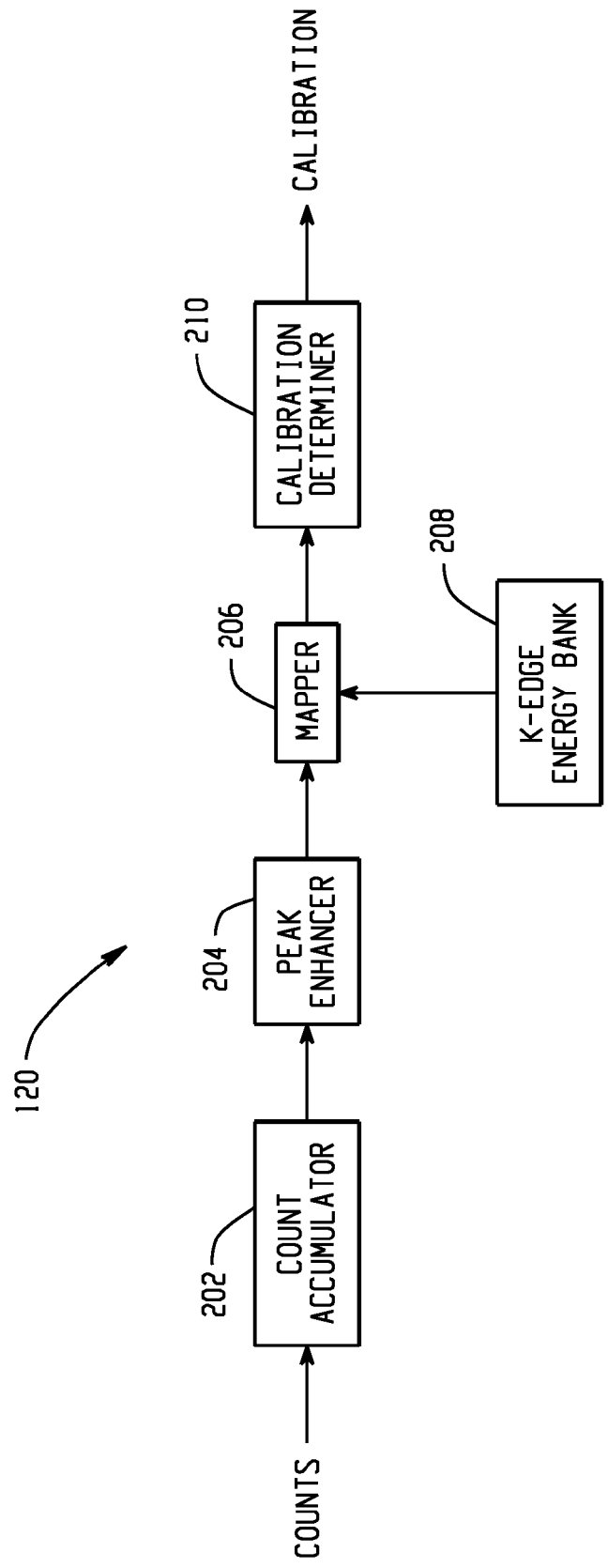
FIG. 2 illustrates a non-limiting example of the calibration component.

Turning to FIG. 2, a non-limiting example of the calibration component 120 is illustrated. The calibration component 120 includes a count accumulator 202, a peak enhancer 204, a mapper 206, a k-edge energy bank 208, and a calibration determiner 210.

For this example, assume that the spectral characteristic is the k-edge energy of the material 136. For explanatory purposes, the following is described in connection with Gadolinium (Gd), which has a k-edge at about 50.2 keV. Other suitable materials 136 include, but are not limited to, silver (Ag: k-edge≈25.5 keV), tin (Sn: k-edge≈29.2 keV), antimony (Sb: k-edge≈30.5 keV), iodine (I: k-edge≈33.2 keV), barium (Ba: k-edge≈37.4 keV), lutetium (Lu: k-edge≈63.3 keV), gold (Au: k-edge≈80.7 keV), lead (Pb: k-edge≈88.0 keV), uranium (U: k-edge≈115.6 keV), or another material with a known k-edge. In general, the thicker the material 136, the more the k-edge is pronounced, and the thinner the material 136, the greater the signal output by the detector. In the illustrated example, the material is about 0.7 mm thick, and the results are for a 100 kVp tungsten x-ray tube.

Figure 3:
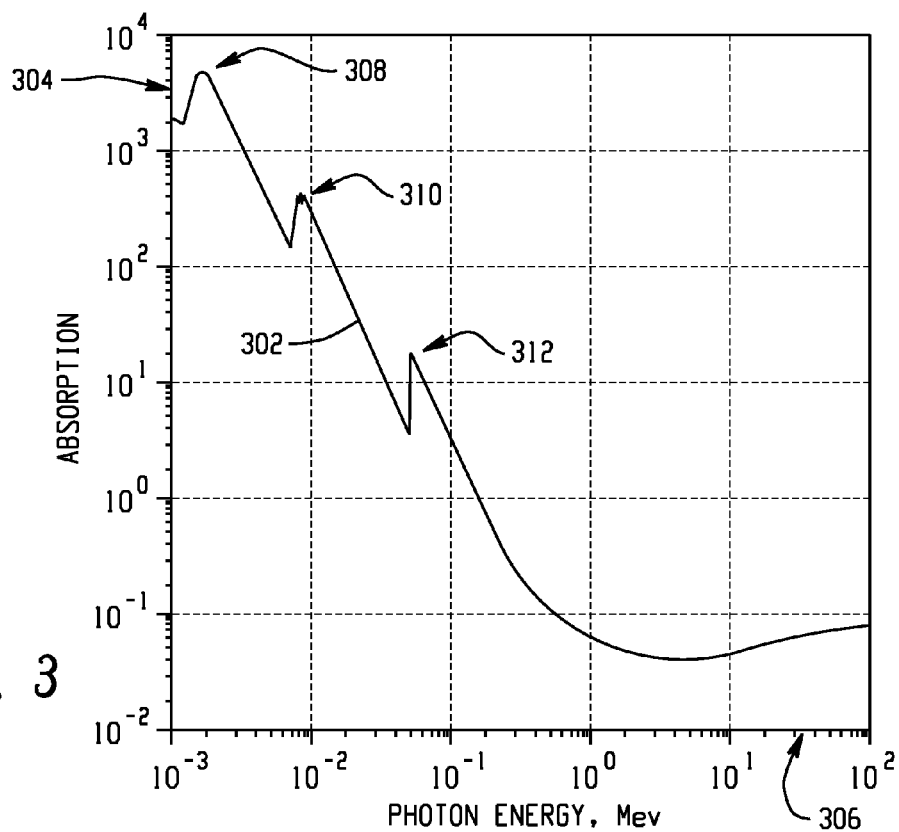
FIG. 3 illustrates a graphical representation of an absorption distribution for photons traversing Gadolinium as a function of photon energy.

Generally, the number of photons absorbed by the material 136 decreases as a function of increasing photon energy. However, photons having energy slightly above the k-edge energy (the k-shell binding energy) of the material 136 are more likely to be absorbed by the material 136 relative to photons having energy just below k-edge energy due to the photoelectric effect. A consequence is that the number of photons absorbed by the material 136 abruptly increases at the k-edge energy. FIG. 3 shows an example absorption distribution 302 for Gd. A first axis 304 represents absorption, and a second axis 306 represents photon energy. The distribution 302 shows that absorption generally decreases as a function of increasing photon energy. However, there are several rising edges 308, 310 and 312, or increases in photon absorption, which correspond to binding energies of the inner layers of electrons. The rising edge 312 falls in the range of energies (e.g., 20 keV-120 keV) within those generally used in diagnostic imaging. This increase in absorption corresponds to the k-edge of Gd, which is at about 50.2 keV.

Figure 4:
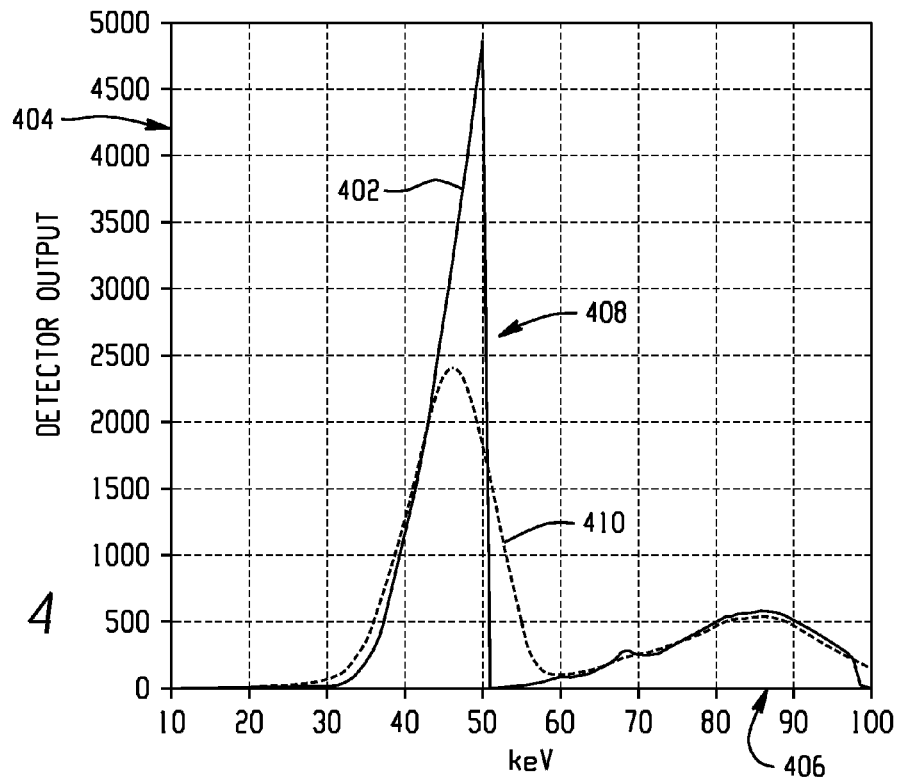
FIG. 4 illustrates a graphical representation of an output signal of a detector pixel detecting radiation traversing Gadolinium as a function of photon energy.

At low energies the intensity measured in the detector array increases with increasing photon energy as higher energy photons are less likely to be absorbed relative to lower energy photons as noted above and the usually filtered emitted spectrum increases in intensity with energy. On the high energy side the measured intensity starts to fall off with energy due to the decreasing intensity in the primary spectrum, which reaches zero intensity at an energy equivalent to the x-ray tube acceleration voltage. The k-edge is identifiable in the detector array output signal as an abrupt decrease in the value of the detector array output signal. The foregoing is graphically illustrated in FIG. 4, which shows an example detector array output signal distribution 402 for Gd. A first axis 404 represents the detector output, and a second axis 406 represents photon energy. The distribution 402 shows that the detector output signal generally increases as a function of increasing photon energy. However, in the range of energies within those generally used in diagnostic imaging, there is an abrupt decrease in the detector output signal as shown at 408. This decrease corresponds to the k-edge of Gd. A second distribution 410, which is the distribution 402 convolved with an assumed detector resolution and dead time effects, is also shown in FIG. 4.

With continuing reference to FIGS. 1 and 2, for calibration purposes, the thresholds for the energy discriminator 116 correspond to a range of values output by the detector array 110. For this example, the range is from about 20 milli-Volts (mV) to about 160 mV. The energy discriminator 116 compares a peak amplitude of the output signal of each pixel of the detector array 110 with the thresholds. The energy discriminator 116 generates an output signal that indicates which, if any, of the thresholds are exceeded by the peak amplitudes. In one instance, the output may be a digital signal that includes a rising or falling edge for a threshold when the peak amplitude of a signal exceeds the corresponding threshold.

The counter 124 increments a count value for each of the thresholds based on the output of the discriminator 116. For example, the count value for a threshold is incremented when the output of the discriminator 116 produces a signal that indicates that the amplitude of the input signal exceeds the corresponding threshold. As such, one or more count values may be incremented for the signal, for example, for one or more thresholds that are crossed. The output of the counter 124 includes a count value for each threshold.

Figure 5:
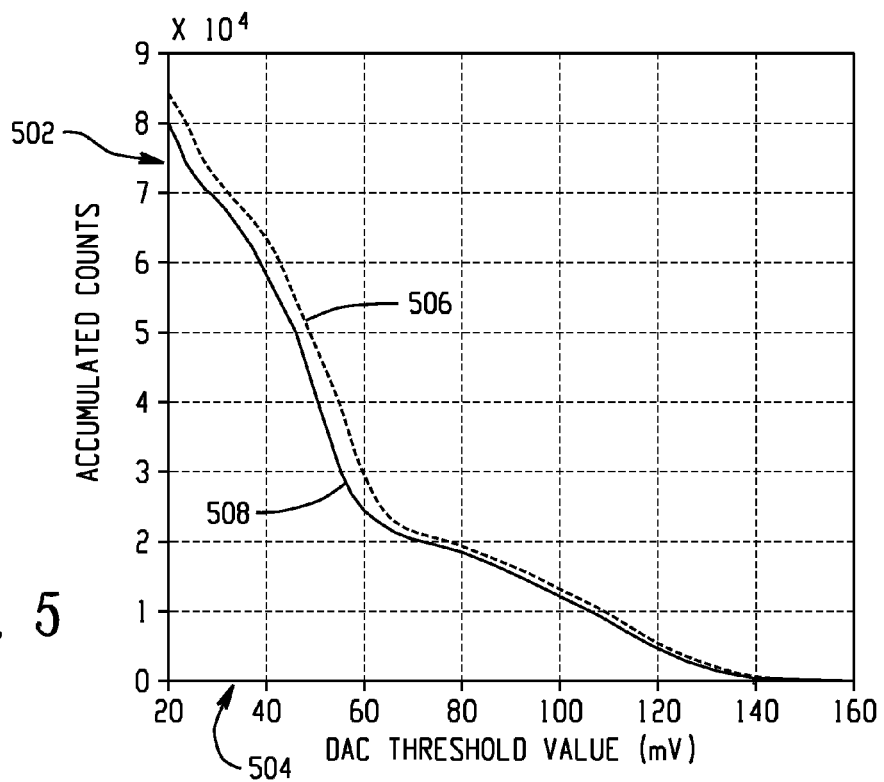
FIG. 5 illustrates a graphical representation of accumulated counts for an output signal of a detector pixel detecting radiation traversing Gadolinium as a function of threshold energy.

The count accumulator 202 accumulates the counts from the counter 124. In one instance, the counts are accumulated as a function of the thresholds. This is shown in FIG. 5, wherein a first axis 502 represents the accumulated count, and a second axis 504 represents the threshold values in mV. A first distribution 506 represents the accumulated counts for a first detector pixel, and a second distribution 508 represents the accumulated counts for a second detector pixel. Note that the distribution 506 and 508 for the two different detector pixels are offset by several mV. This may be due to different performance such as different gain and/or offset, of the detector and its channels.

Figure 6:
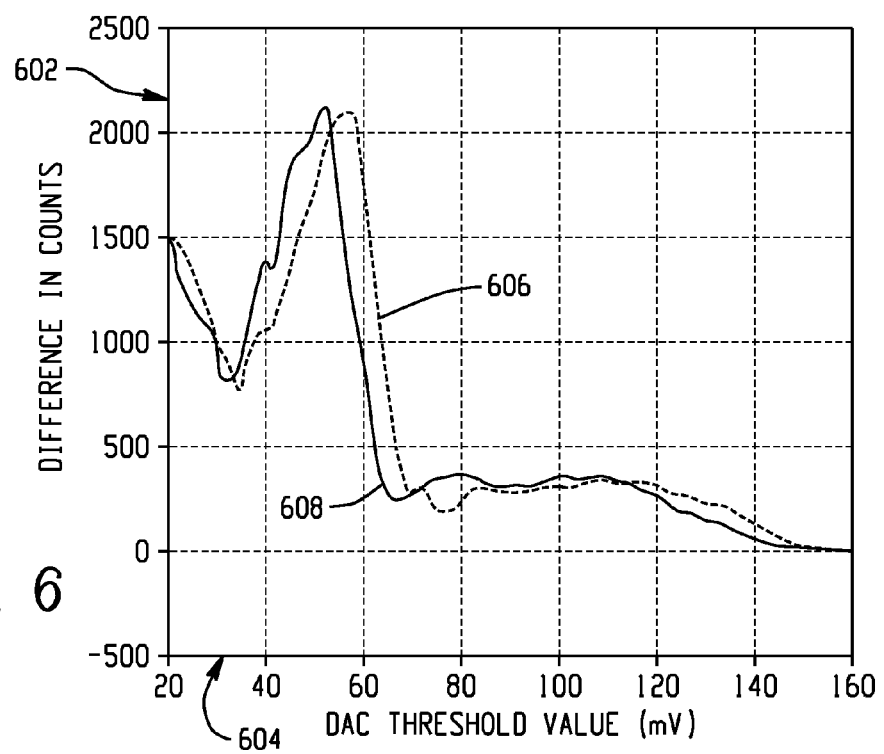
FIG. 6 illustrates a graphical representation of showing a k-edge in the accumulated counts.

With continuing reference to FIGS. 1 and 2, the peak enhancer 204 enhances a peak indicative of the k-edge in the accumulated counts. In one instance, this is achieved by differentiating the accumulated count distribution to identify the maximum value in the differentiated distribution. FIG. 6 shows an example in which a first axis 602 represents the differentiated count, and a second axis 604 represents the threshold values. A first distribution 606 shows the distribution of differentiated counts for the first detector pixel, and a second distribution 608 shows the distribution of differentiated counts for the second detector pixel. The peak positions in the differentiated distributions correlate to the maximum in 410 of FIG. 4, which is a few keV below the k-edge energy. The position of the k-edge can be found in 410 of FIG. 4 and in 606 and 608 of FIG. 6 as the energy positions of the steepest decrease in the respective curves. The steep descent can be easily found as the maximum value of the negative first derivative of the curves. Due to noise in the data some smoothing may have to be applied. Note that the distributions 606 and 608 in FIG. 6 peak within a couple keV of the k-edge energy of Gd.

The mapper 206 maps the peak in the differentiated accumulated counts distributions 606 and 608 to the corresponding k-edge of the material 136, which correlates the k-edge energy to a threshold value. A k-edge bank 208 includes the k-edge energy of various materials. The mapper 206 maps the peak to the appropriate k-edge energy based on the type of the material 136 and the corresponding k-edge energy in the k-edge bank 208. In the illustrated example, the first detector pixel peak, which corresponds to a threshold value of about 57.5 mV, is correlated with the Gd k-edge energy 50.2 keV, and the second detector pixel peak, which corresponds to a threshold value of about 62.5, is also correlated with 50.2 keV.

The calibration determiner 210 determines the calibration 118 for each detector pixel based on the output of the mapper 206. In general, at least two mapping (data points) for each detector pixel using at least two different materials, each with a different but known k-edge energy, are used to determine the calibration 118. With two data points, a linear fit is used to correlate a desired energy level with an appropriate threshold value. With more than two data points, a higher order technique, such as a quadratic or a cubic fit, can be used. In one instance, the calibration 118 includes a look-up table (LUT) that provides a output signal to energy mappings for the diagnostic imaging range. In another instance, the data points are coefficients of a polynomial function. Mappings between and outside of the data points can be determined via interpolation or extrapolation and/or otherwise.

It is to be appreciated that a radioactive material may be used in addition to the generated radiation beam to determine at least one data point for the calibration 118.

In an alternative approach, if the spectral response of the detector is known, the energy spectrum of the detector can be convolved with the respective spectral response and the result can be compared to the measured spectra.

Figure 7:
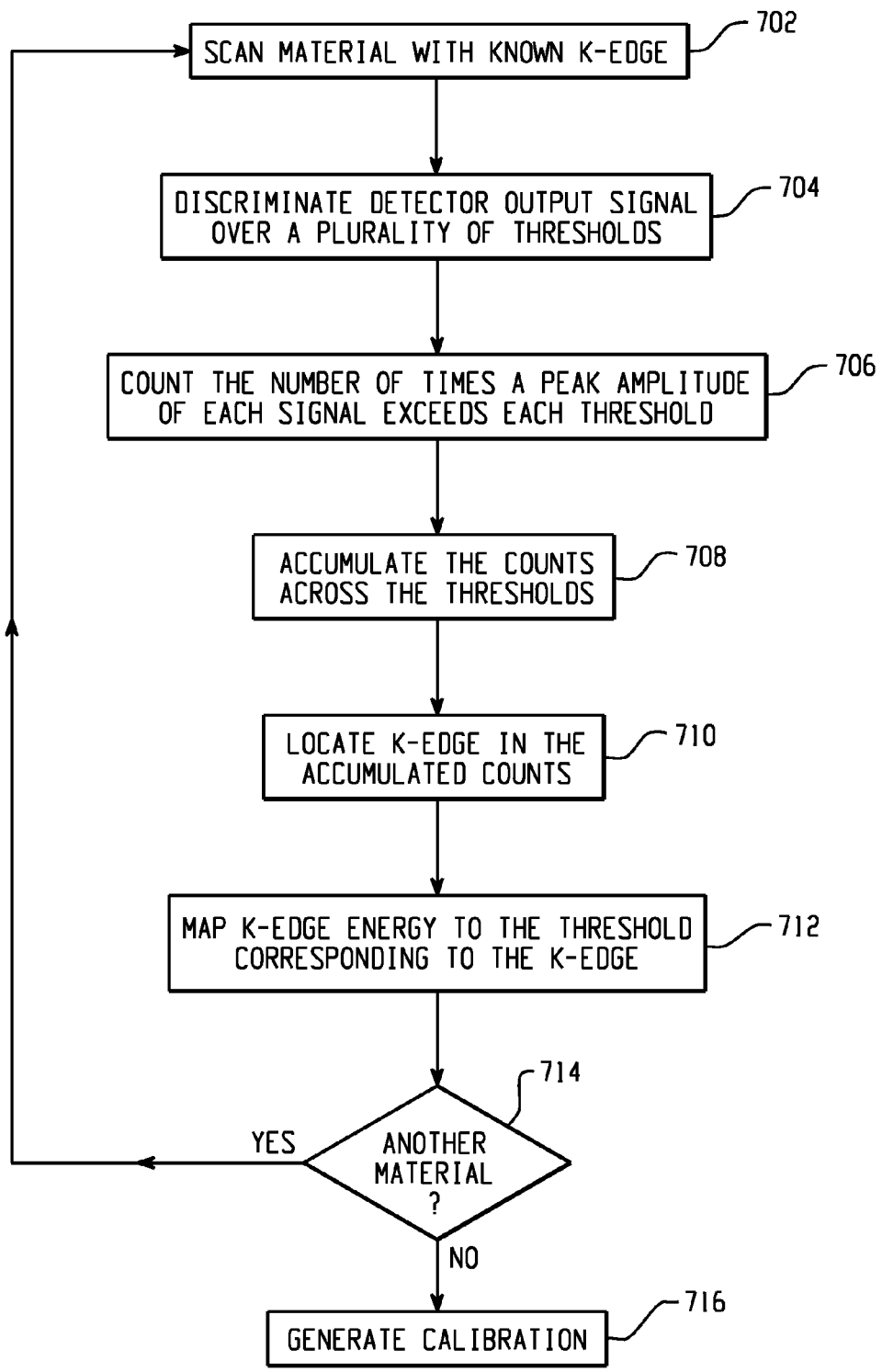
FIG. 7 illustrates a method.

The calibration is now described in connection with FIG. 7.

At 702, a material with a known k-edge energy is scanned.

At 704, an output signal of a detector pixel detecting a photon traversing the material is discriminated across a plurality of different thresholds representing values in a range of values output by the detector pixel.

At 706, for each threshold, a count is incremented when an amplitude of the output signal exceeds a corresponding threshold.

At 708, the counts are accumulated across the thresholds.

At 710, the k-edge for the material is located in the accumulated count distribution, for example, by differentiating the accumulated count distribution.

At 712, the threshold value corresponding to the k-edge is mapped to the k-edge energy of the material.

At 714, steps 702-712 are performed at least a second time using a second material with a different known k-edge energy.

At 716, the mappings are used to generate the calibration 118, which is used during scanning to correlate the output signal of a detector pixel with an energy of a detected photon.

Figure 8:
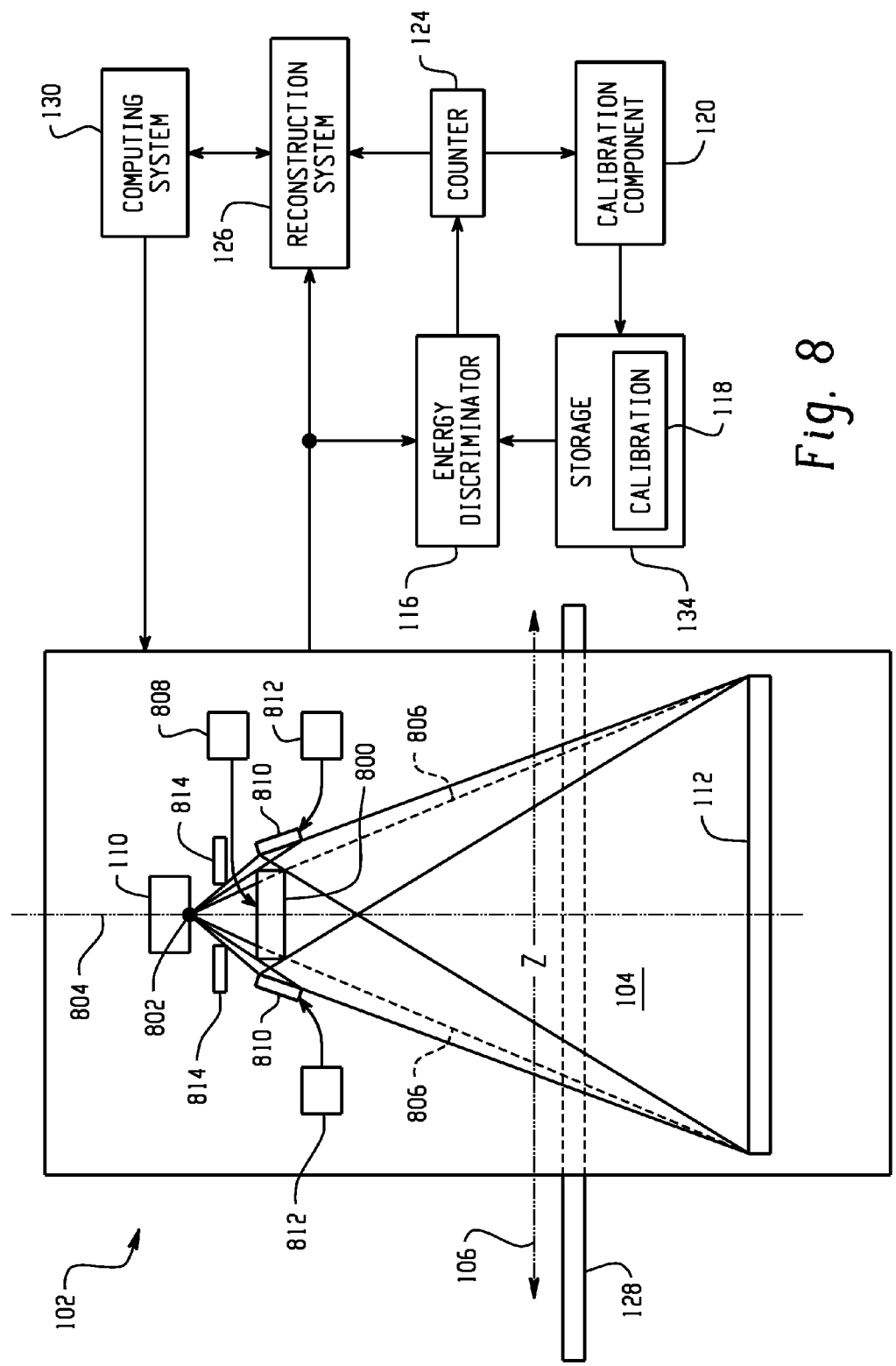
FIG. 8 illustrates another example system including a detector calibration component.

FIG. 8 illustrates another embodiment for determining the calibration 118. For this embodiment, fluorescence radiation of known energy is used to determine the calibration 118.

In the illustrated example, a radiation or beam block 800 is moveably affixed to the scanner 100 via a bearing or the like and is configured to move between a first or calibration position in which it is located between a focal spot 802 of the radiation source 110 and the detector array 112 (as shown) and at least one non-calibration (scanning) position in which it is not located between the focal spot 802 and the detector array 112 (not shown). For this example, the focal spot 802 is located on imaginary axis 804 that extends perpendicular to and cuts through a central region of the detector array 112.

When at the calibration position, the beam block 800, which includes a high Z material such as lead or other high Z material, blocks radiation emitted from the focal spot 802. In one instance, this includes attenuating emitted radiation so that substantially no transmission (direct) radiation illuminates the detector array 112. The region between dotted lines 806 shows the portion of the radiation beam blocked by the beam block 800. When the beam block 800 is at the non-calibration position (not shown), transmission radiation traverses the examination region 104, and any object or subject therein, and illuminates the detector array 112, as shown by the dotted lines 806.

A beam block controller 808 controls a drive apparatus, such as a motor or the like, which is mechanically coupled to the bearing and which moves the bearing and, hence, the beam block 800. Such movement can be in and out of calibration and scanning positions such as the first position and the non-calibration position noted above.

For calibration purposes, at least one target 810 is located in the path of rays that are not blocked by the beam block 800 and that do not directly illuminate the detector array 112. Two targets 810, on opposing sides of the beam block 800 along the z-axis direction, are shown for explanatory purposes. In the illustrated embodiment, the targets 810 are affixed to and part of the scanner 100 and, as shown, can be oriented or angled along the z-axis so that the radiation emitted therefrom traverses paths that illuminate the detector array 112.

The targets 810 include one or more materials that fluoresce or emit radiation having a known spectrum or emission lines in response to being struck by radiation. At least one of the targets 810 includes at least two materials or an alloy of materials that provide sufficient emission lines for low energy and for high energy. Such a target 810 may be moveably affixed to the scanner 100 and configured to be selectively moved between a first position in which one of the materials is in the radiation path and a second position in which another one of the material is in the radiation path.

Figure 9:
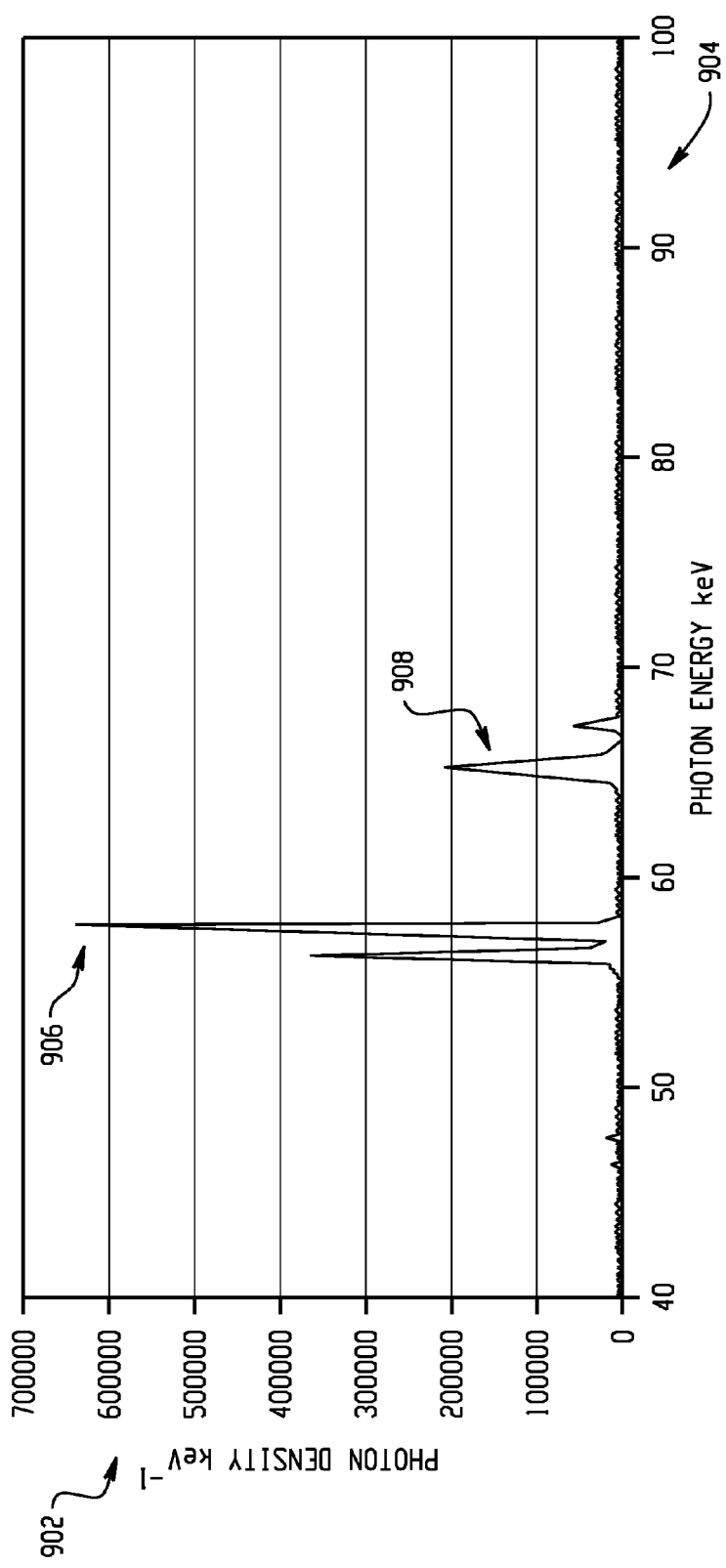
FIG. 9 illustrates an example x-ray fluorescence emission spectrum.

Examples of target materials include, but are not limited to, silver ($K_{\alpha 1}$~22.2 keV), Tantalum, ($K_{\alpha 1}$~57.0 keV), gold ($K_{\alpha 1}$~68.8 keV), and lead ($K_{\alpha 1}$~75.0 keV), and/or other materials. FIG. 9 shows example emission lines for Tantalum. A first or y-axis 902 represents photon density (in units of $keV^{-1}$), and a second or x-axis 904 represents photon energy (in units of keV). A first set of emission lines or doublets 906 corresponds to K-alpha ($K_{\alpha}$) emission lines ($K_{\alpha 1}$ and $K_{\alpha 2}$), which result when electrons transition to the "K" shell from a 2p orbital of the "L" shell, and each line corresponds to a slightly different energy, depending on spin-orbit interaction energy between the electron spin and the orbital momentum of the 2p orbital. A second set of emission lines or doublets 908 corresponds to K-beta ($K_{\beta}$) emission lines ($K_{\beta 1}$ and $K_{\beta 2}$), which result when electrons transition to the "K" shell from a 2p orbital of the "M" shell.

Returning to FIG. 8, where the target 810 is moveably affixed to the scanner 100, a target controller 812 controls a drive apparatus such as a motor or the like that moves the target 810. As noted above, such movement may includes moving the target 810 between a first position in which one of the materials is in the radiation path and a second position in which the material is in the radiation path. Such movement may also include moving the target 810 in and out of the radiation path.

A collimator 814 collimates the radiation emitted from the focal spot 802 to form a radiation beam with a suitable z-axis beam angle, or width. In the illustrated example, this includes collimating the emitted radiation so that the resulting radiation beam illuminates the targets 810. For non-calibration purposes, the collimator 814 can collimate the radiation emitted so that radiation does not illuminate the targets 810, while illuminating a suitable region of the detector array 112.

As discussed above, the detector array 112 detects the radiation striking the detector array 112, which, in this example, includes the radiation emitted by the targets 810, and generates a signal having an amplitude peak(s) that is indicative of the energy of the detected radiation. The energy discriminator 116 energy discriminates the signal based on the one or more energy thresholds and generates an output signal that indicates which, if any, of the thresholds is exceeded by the peak amplitudes. The counter 124 increments a count value for each of the thresholds based on the output of the discriminator 116.

Figure 10:
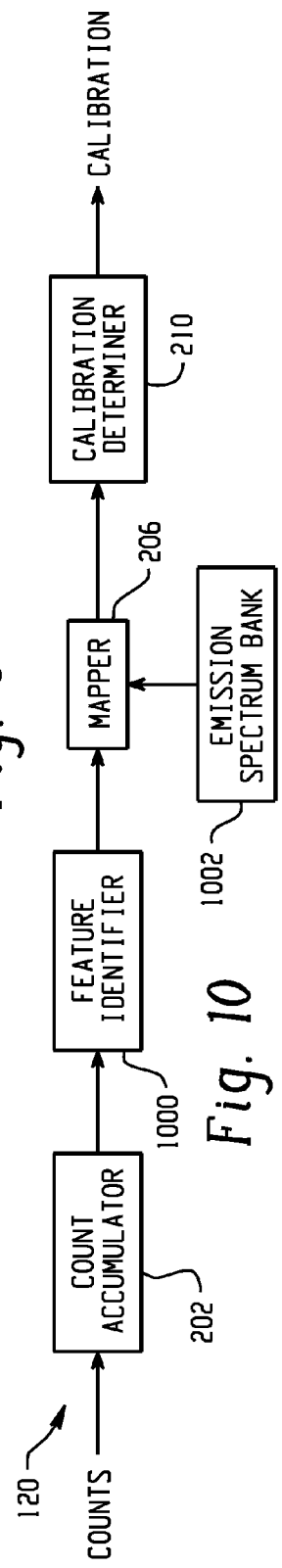
FIG. 10 illustrates another non-limiting example of the calibration component.

As shown in FIG. 10, in this embodiment the calibration component 120 includes the count accumulator 202, which, as discussed above, accumulates the counts from the counter 124, for example, to produce a count distribution as a function of energy.

A feature identifier 1000 identifies at least one feature indicative of the energy of the detected radiation from the count distribution. For example, the feature identifier 1000 may identify a peak amplitude of one or more spikes or pulses in the count distribution, a fast rise or fall in amplitude exceeding a corresponding threshold value, and/or other information. With respect to FIG. 9, the feature identifier 1000 may identify one, two, three or all four of the peaks, and/or other information.

The mapper 206 maps the identified peak(s) and/or other information with corresponding emission spectrums stored in an emission spectrum bank 1002. For instance, the mapper 206 can map an energy associated with a peak amplitude to the appropriate emission spectrum based on the type of the target material and the corresponding emission spectrum in emission spectrum bank 1002.

The calibration determiner 210 determines the calibration 118 for a detector pixel based on the output of the mapper 206. In general, at least two mappings or data points for a detector pixel are obtained and used to determine the calibration 118. With two data points, a linear fit can be used to correlate a desired energy level output by the detector array 112 with an appropriate threshold value. With more than two data points, a higher order technique, such as a quadratic or a cubic fit, can be used. Data points outside of the range of the obtained data points can be determined via extrapolation and/or otherwise.

As discussed above, the calibration 118 can be stored in the storage 134 and/or otherwise, and used during normal (non-calibration) operation of the scanner 100.

Figure 11:
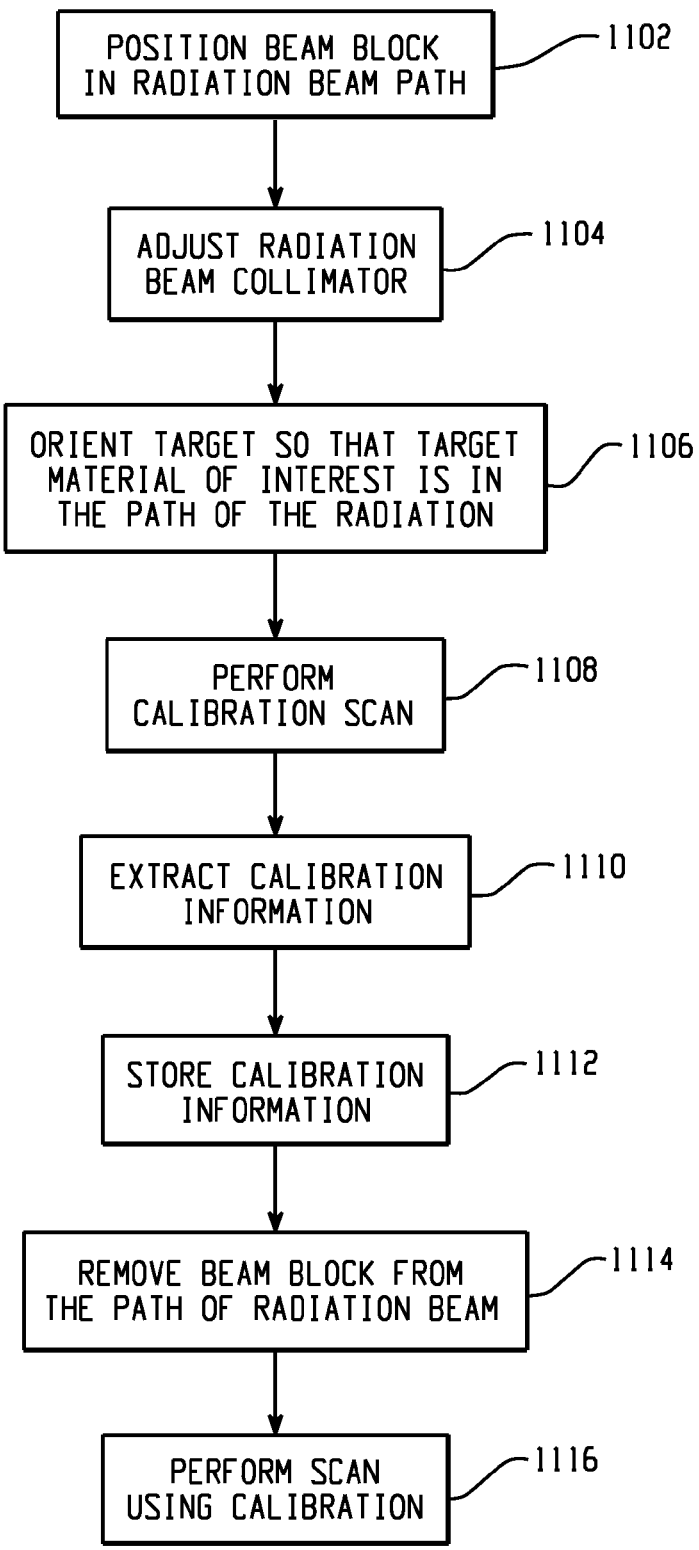
FIG. 11 illustrates another method.

FIG. 11 illustrates a calibration method. At 1102, the beam block 800 is positioned in the path between the focal spot 802 and the detector array 112. At 1104, the radiation beam is collimated so that radiation emitted from the focal spot 802 illuminates the targets 810. At 1106, the targets 810 are suitably oriented for a measurement using a desired target material. At 1108, a calibration scan is performed. At 1110, the calibration information is extracted from the scan data. Steps 1106-1110 can be repeated for one or more other target material. At 1112, the calibration information is stored. At 1114, the beam block 800 is moved out of the path between the focal spot 802 and the detector array 112. At 1116, the calibration information can be used with non-calibration (normal) scans.

Variations of the embodiment of FIG. 8 are discussed.

In another embodiment, the system 100 is configured to automatically perform the calibration based on a pre-determined calibration schedule (e.g., weekly, monthly, etc.), on-demand, based on a number of scans, and/or otherwise.

In the above embodiment, the calibration components, for example, the beam block 800 and the targets 810 are affixed to the system. In another embodiment, a field technician or other personal installs these components for the calibration and removes them thereafter.

In the above example, the target 810 includes at least two materials, one low energy emitter and one high energy emitter. In another embodiment, at least two physically different targets, one low energy emitter and one high energy emitter, are used. With this embodiment, the targets 810 are interchangeable or exchangeable via the controller 812, manually, and/or otherwise.

In another embodiment, more than two target materials, for example, at least three target materials with different emission spectrums, are used.

As illustrated, the radiation beam generated by the target 810 illuminates substantially the entire detector array 112. In other embodiments, a smaller region of the detector array 112 may be illuminated. With such an embodiment, more than one scan using the same target material and covering different regions of the detector array 112 may be performed, and the resulting data may be combined to produce data for the entire detector array 112, if desired. Otherwise, data for regions of the detector array 112 not illuminated during calibration can be otherwise determined.

Figure 12:
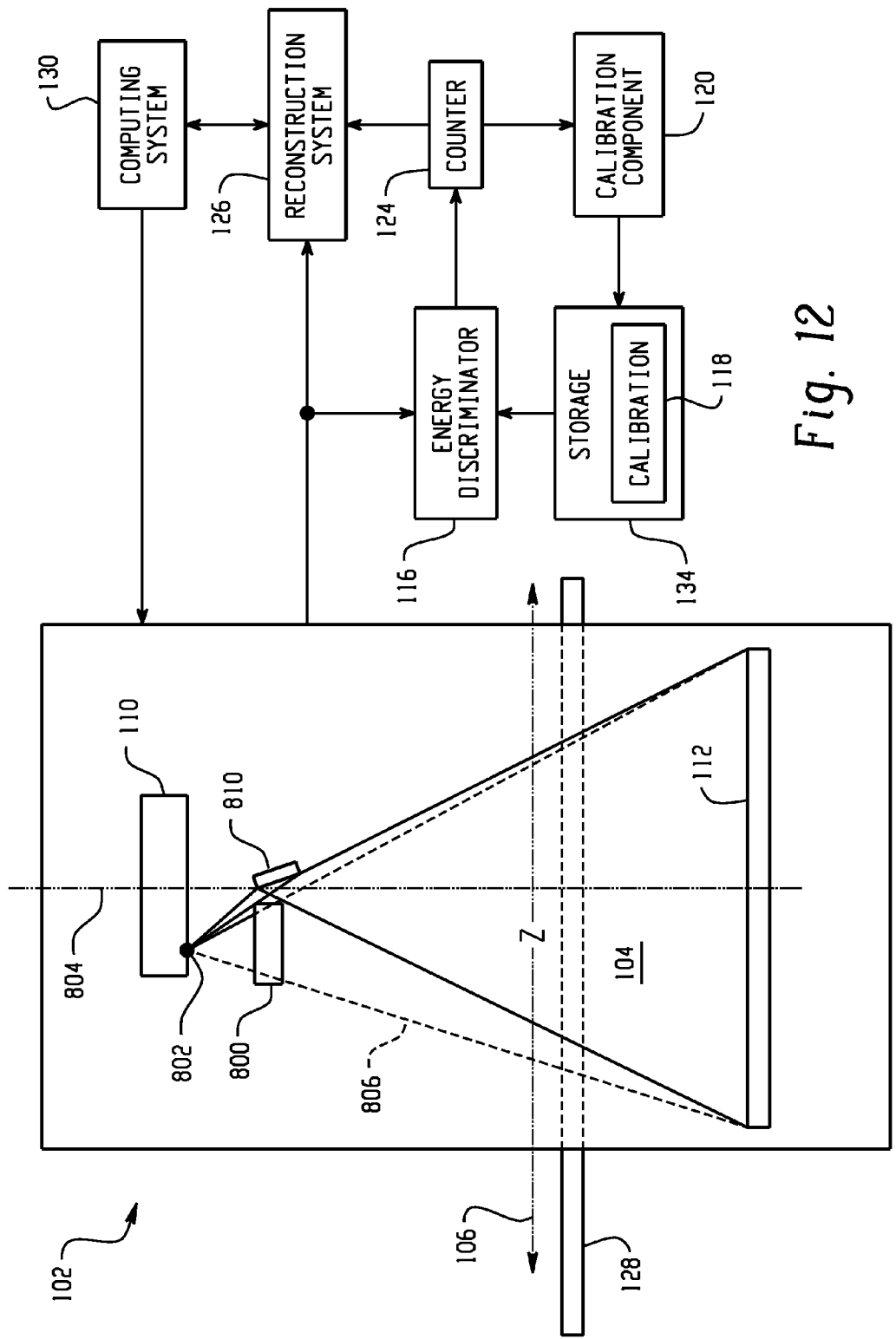
FIG. 12 illustrates another example system including a detector calibration component.

In FIG. 12, the focal spot 802, at least for calibration purposes, is located offset (e.g., 10 to 30 mm) from the axis 804 along the z-axis. The focal spot 802 can be positioned as such electromagnetically or electro-statically (depending on the radiation source technology), and/or by physically manually or automatically translating the radiation source 110. In this example, a single target 810, for calibration purposes, is located on or near the axis 804. Again, the beam block 800 is positioned to block transmission radiation that would otherwise strike the detector array 112, but allow radiation to strike the target 810. This embodiment generally is well-suite for use with two-dimensional anti-scatter grids.

The techniques described herein can be combined such that the calibration is determined based on a combination of fluorescent, characteristic and/or radioactive radiation. As such, in one instance a filtered spectrum provides a high or low energy feature, and the fluorescence radiation provides the other feature. In another instance, the characteristic radiation of the radiation source 110 is used as one of the calibration lines, and the filtered spectrum or the fluorescence radiation provides the other feature. In yet another instance, the high-energy cut-off of the spectrum, which is given by the radiation source acceleration voltage, may be used as high-energy calibration point.

In all cases mentioned above, where two subsequent measurements are used, the radiation source voltage and/or current can be adjusted, and spectral filtering can be applied.

It is to be appreciated that the techniques described herein may be implemented by way of computer readable instructions embodied and/or encoded in a computer readable storage medium, which, when executed by a computer processor (s), cause the processor(s) to carry out the acts described herein. By way of non-limiting example, the computer system 130 may execute the instructions to carry out the acts described herein. This may include positioning a suitable material in the radiation path, scanning the material, and generating the calibration from radiation traversing the material and illuminating a detector pixel, and repeating these steps at least once.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

We claim:

1. A method, comprising:
   detecting generated radiation that traverses a material having a known spectral attenuation or fluorescence characteristic with a radiation sensitive detector pixel that outputs a signal indicative of the detected radiation,
   wherein the radiation is generated by an imaging system, the material is located in a filter tray of the imaging system, and the filter tray is movable to selectively move the material into and out of the generated radiation;
   counting a number of times a peak amplitude of the output signal exceeds each of a plurality of different thresholds corresponding to an output range of the detector pixel; and
   determining a mapping between the output signal of the pixel and the known spectral characteristic, wherein the mapping is based on a distribution of the counts over the output range.

2. The method of claim 1, further including determining an energy of a photon detected by the radiation sensitive detector pixel based on a corresponding output of the radiation sensitive detector pixel and the mapping.

3. The method of claim 1, further including locating the spectral characteristic in the distribution based on an accumulation of the counts over the output range.

4. The method of claim 1, further including differentiating the distribution one or times to identify a peak in the differentiated distribution that corresponds to the spectral characteristic.

5. The method of claim 1, further including:
comparing a peak amplitude of the output signal with a plurality of different thresholds that represent an output range of the detector pixel;
counting a number of times the peak amplitude exceeds each of the thresholds; and
mapping the output signal of the pixel and the known spectral characteristic based on a distribution of an accumulation of the counts over the output range.

6. The method of claim 1, wherein the signal is indicative of an energy of a detected photon.

7. The method of claim 1, wherein the spectral characteristic is a k-absorption edge of the material.

8. The method of claim 1, wherein the material includes one of silver, tin, gadolinium, antimony, iodine, barium, lutetium, gold, lead, bismuth, or uranium.

9. An imaging system, comprising:
a radiation source that emits radiation that traverses an examination region;
a tray located near the radiation source, wherein the tray includes a material with known spectral characteristics, and the tray is movable to selectively position the material in a path of the emitted radiation;
a spectral detector that detects radiation that traverses the material and the examination region;
a calibration component that calibrates the spectral detector based on the detected radiation;
a count accumulator that accumulates counts representing a number of times a peak value of the output signal exceeds each of a plurality of different threshold values; and
a mapper that maps a peak value of the accumulated counts to a k-edge energy of the material, wherein the calibration component generates a calibration for the spectral detector based on the mapping.

10. The imaging system of claim 9, wherein the material has a known k-edge, and the detector outputs a signal indicative of the energy of detected radiation, and wherein the calibration component generates a calibration based on the k-edge of the material and the output value of the spectral detector.

11. The imaging system of claim 9, wherein the calibration component further includes:
a peak enhancer that enhances the peak value of the accumulated counts prior to the mapping.

12. The imaging system of claim 11, wherein the peak enhancer differentiates the accumulated counts to enhance the peak value of the accumulated counts.

13. The imaging system of claim 9, further including:
an energy discriminator that energy discriminates the output signal based the thresholds; and
a counter that counts a number of times the peak value of the output signal exceeds a threshold, for each of the thresholds.

14. A method for calibrating a detector array of an imaging system, comprising:
detecting fluorescence radiation having a known spectral characteristic with a radiation sensitive detector pixel of the detector array, which outputs a signal indicative of an energy of the detected fluorescence radiation;
determining a mapping between the output signal and the known spectral characteristic; wherein the mapping is based on a distribution of counts over an output range of a detector pixel detecting the radiation; and
determining a calibration for the detector array of the imaging system based on the mapping.

15. The method of claim 14, further including:
generating the fluorescence radiation by irradiating a material having the known spectral characteristic with x-radiation, wherein the material emits the fluorescence radiation.

16. The method of claim 15, further including:
employing the calibration to set at least one energy threshold of a photon energy-discriminator of the system.

17. The method of claim 14, further including:
determining a feature of the output signal, wherein the feature is indicative of the energy of the detected fluorescence radiation; and
mapping the feature to the known spectral characteristic.

18. The method of claim 17, wherein the feature includes at least one of a peak amplitude of an emission distribution of the detected fluorescence radiation, an amplitude increase in the distribution greater than a first threshold, or an amplitude decrease in the distribution greater than a second threshold.

19. The method of claim 14, further including generating the fluorescence radiation by alternatively illuminating at least one high energy emitter with radiation produced by an x-ray tube of the imaging system and at least one low energy emitter with radiation produced by an x-ray tube of the imaging system.

20. The method of claim 19, further including:
generating a calibration curve based on a first mapping using a first output signal of the detector array corresponding to the at least one low energy emitter and on a second mapping using a second output signal of the detector array corresponding to the at least one high energy emitter.

21. An imaging system, comprising:
a radiation source that emits first radiation that traverses an examination region;
a detector array that detects the first radiation and generates a signal indicative thereof;
a detector calibration apparatus; including:
a radiation block that blocks the first radiation from illuminating the detector array; and
at least one target that receives the first radiation and generates second radiation that includes a known spectral characteristic and that illuminates the detector array; and
a calibration component that generates a calibration for the detector array based on an identified known spectral characteristic of the second radiation and a pre-determined spectral characteristic of the target.

22. The system of claim 21, further including:
a feature identifier that identifies the known spectral characteristic in the second radiation.

23. The system of claim 21, wherein the calibration correlates the identified spectral characteristic and the pre-determined spectral characteristic.

24. The system of claim 21, wherein the identified spectral characteristic includes at least one of a peak amplitude of an emission distribution corresponding to the second radiation, an amplitude increase in the distribution greater than a first threshold, or an amplitude decrease in the distribution greater than a second threshold.

25. The system of claim 21, wherein the radiation block is selectively moveable between a first position at which it blocks the transmission radiation and at least a second position at which it does not block the transmission radiation.

26. The system of claim 21, wherein the target includes at least two materials, each having a different spectral characteristic.

27. The system of claim 26, wherein the at least two materials are alternately positioned in a path of the first radiation, and a first spectral characteristic is identified for one of the at least two materials and a second spectral characteristic is identified for another of the at least two materials, and the calibration component generates the calibration based on the first and second spectral characteristics.

28. A system, comprising:

a detector calibration apparatus; including:

a radiation block that blocks first radiation from illuminating a detector array, wherein the first radiation is emitted by a radiation source and traverses an examination region and the detector array detects the first radiation and generates a signal indicative thereof; and at least one target that receives the first radiation and generates second radiation that includes a known spectral characteristic and that illuminates the detector array; and a calibration component that generates a calibration for the detector array based on an identified known spectral characteristic of the second radiation and a pre-determined spectral characteristic of the target.

29. The apparatus of claim 28, wherein the radiation block and/or the target is removably mounted to the system when calibrating the detector array and removed from the system when scanning an object or subject.

30. The apparatus of claim 28, wherein the target includes at least two materials that emit radiation having a different known spectral characteristics.

* * * * *